(12) United States Patent
Bowman

(10) Patent No.: US 12,310,754 B2
(45) Date of Patent: May 27, 2025

(54) CATHETER CIRCUIT

(71) Applicant: MicroVention, Inc., Aliso Viejo, CA (US)

(72) Inventor: Heath Bowman, Aliso Viejo, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 723 days.

(21) Appl. No.: 17/644,317

(22) Filed: Dec. 14, 2021

(65) Prior Publication Data

US 2022/0104770 A1 Apr. 7, 2022

Related U.S. Application Data

(63) Continuation of application No. 15/169,588, filed on May 31, 2016, now Pat. No. 11,229,402.

(Continued)

(51) Int. Cl.
| | |
|---|---|
| *A61B 5/00* | (2006.01) |
| *A61B 17/12* | (2006.01) |
| *A61M 25/00* | (2006.01) |
| *A61B 5/145* | (2006.01) |
| *A61B 17/00* | (2006.01) |

(52) U.S. Cl.
CPC ........ *A61B 5/6852* (2013.01); *A61B 17/1214* (2013.01); *A61B 5/14542* (2013.01); *A61B 5/6851* (2013.01); *A61B 5/6876* (2013.01); *A61B 2017/00022* (2013.01); *A61B 2017/12054* (2013.01); *A61B 2017/12068* (2013.01); *A61B 2560/063* (2013.01);

(Continued)

(58) Field of Classification Search
CPC ............ A61B 5/6852; A61B 2562/221; A61B 2562/222; A61B 2562/227; A61M 25/005; A61M 25/0051; A61M 25/0012
See application file for complete search history.

(56) References Cited

U.S. PATENT DOCUMENTS

| 4,274,423 A | 6/1981 | Mizuno et al. |
|---|---|---|
| 4,484,586 A | 11/1984 | McMickle et al. |

(Continued)

FOREIGN PATENT DOCUMENTS

| CN | 102065779 A | 5/2011 |
|---|---|---|
| CN | 104224112 A | 12/2014 |

(Continued)

OTHER PUBLICATIONS

European Patent Office, Extended European Search Report dated Sep. 15, 2023 in European Patent Application No. 23174406.1, 8 pages.

(Continued)

*Primary Examiner* — Devin B Henson
(74) *Attorney, Agent, or Firm* — Inskeep IP Group, Inc.

(57) ABSTRACT

A circuit system includes a user interface, voltage source, and a terminal bank connected to the voltage source. The circuit can be used in a powered catheter system where the catheter includes a structural reinforcement layer such as a braid comprised of one or more wires. The reinforcement layer can be used to convey a current or signal in a powered catheter. The catheter may utilize a hypotube element which provides integrated sensors in order to power and control multiple systems in the powered catheter.

19 Claims, 13 Drawing Sheets

Related U.S. Application Data

(60) Provisional application No. 62/168,525, filed on May 29, 2015.

(52) U.S. Cl.
CPC . *A61B 2562/0247* (2013.01); *A61B 2562/222* (2013.01); *A61M 25/0051* (2013.01)

(56) References Cited

U.S. PATENT DOCUMENTS

| | | | |
|---|---|---|---|
| 5,522,836 A | 6/1996 | Palermo | |
| 5,555,618 A | 9/1996 | Winkler | |
| 5,591,142 A | 1/1997 | Van Erp | |
| 5,706,809 A | 1/1998 | Littmann et al. | |
| 7,351,914 B2 | 4/2008 | Kaneto et al. | |
| 7,879,030 B2 | 2/2011 | Paul et al. | |
| 8,016,799 B2 | 9/2011 | Nash et al. | |
| 8,560,086 B2 * | 10/2013 | Just | A61B 18/1492 607/101 |
| 8,734,437 B2 * | 5/2014 | Anderson | A61B 5/0215 604/509 |
| 8,814,824 B2 | 8/2014 | Kauphusman et al. | |
| 2003/0120271 A1 | 6/2003 | Burnside et al. | |
| 2003/0222325 A1 | 12/2003 | Jacobsen et al. | |
| 2005/0091833 A1 | 5/2005 | Kiepen et al. | |
| 2006/0004286 A1 | 1/2006 | Chang et al. | |
| 2006/0069346 A1 * | 3/2006 | Smith | A61M 25/005 604/95.05 |
| 2006/0074318 A1 | 4/2006 | Ahmed et al. | |
| 2006/0217791 A1 | 9/2006 | Spinka et al. | |
| 2007/0219551 A1 * | 9/2007 | Honour | A61B 5/6852 606/41 |
| 2009/0163780 A1 | 6/2009 | Tieu | |
| 2009/0177261 A1 | 7/2009 | Teoh et al. | |
| 2010/0049165 A1 | 2/2010 | Sutherland et al. | |
| 2010/0057174 A1 | 3/2010 | Harrison et al. | |
| 2010/0094395 A1 | 4/2010 | Kellett | |
| 2012/0116442 A1 | 5/2012 | Monstadt et al. | |
| 2013/0096455 A1 | 4/2013 | Kassab et al. | |
| 2013/0261656 A1 | 10/2013 | Lorenzo | |
| 2014/0135737 A1 | 5/2014 | Sutherland et al. | |
| 2014/0371563 A1 | 12/2014 | Lichtenstein | |
| 2015/0173773 A1 | 6/2015 | Bowman et al. | |
| 2017/0164867 A1 | 6/2017 | Kassab et al. | |
| 2019/0163780 A1 | 5/2019 | Ozcaglar et al. | |

FOREIGN PATENT DOCUMENTS

| | | |
|---|---|---|
| EP | 2896383 A1 | 7/2015 |
| JP | 2002537885 | 11/2002 |
| JP | 2005533530 | 11/2005 |
| JP | 2011509119 | 3/2011 |

OTHER PUBLICATIONS

Office Action dated Jun. 16, 2020 with English translation in Japanese Patent Application No. 2018-514943.

European Patent Office, Supplementary Extended European Search Report dated Jan. 15, 2019 in European Patent Application No. 16804263.8, 3 pages.

WIPO, U.S. International Search Authority, International Search Report and Written Opinion mailed Aug. 30, 2016 in International Patent Application No. PCT/US2016/035106, 10 pages.

Chinese Patent Office, Office Action dated Aug. 11, 2022 with English translation in Chinese Patent Application No. 202110510520. 7, 14 pages.

* cited by examiner

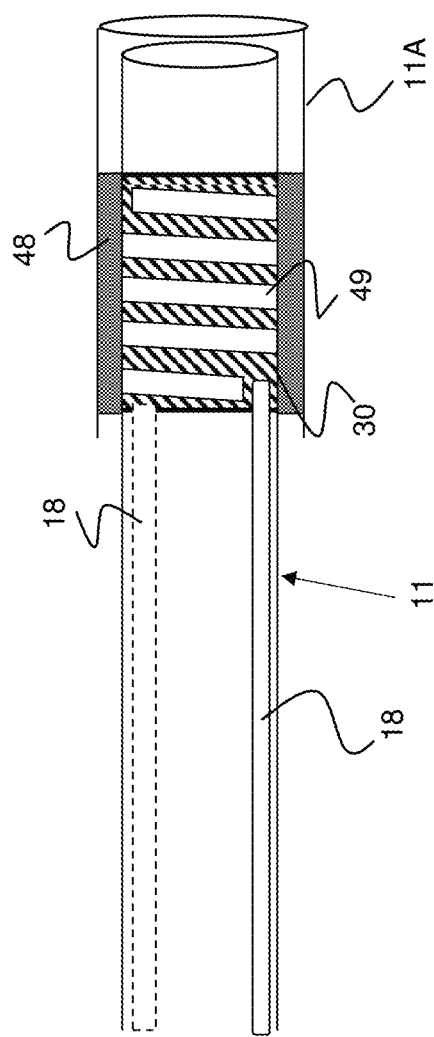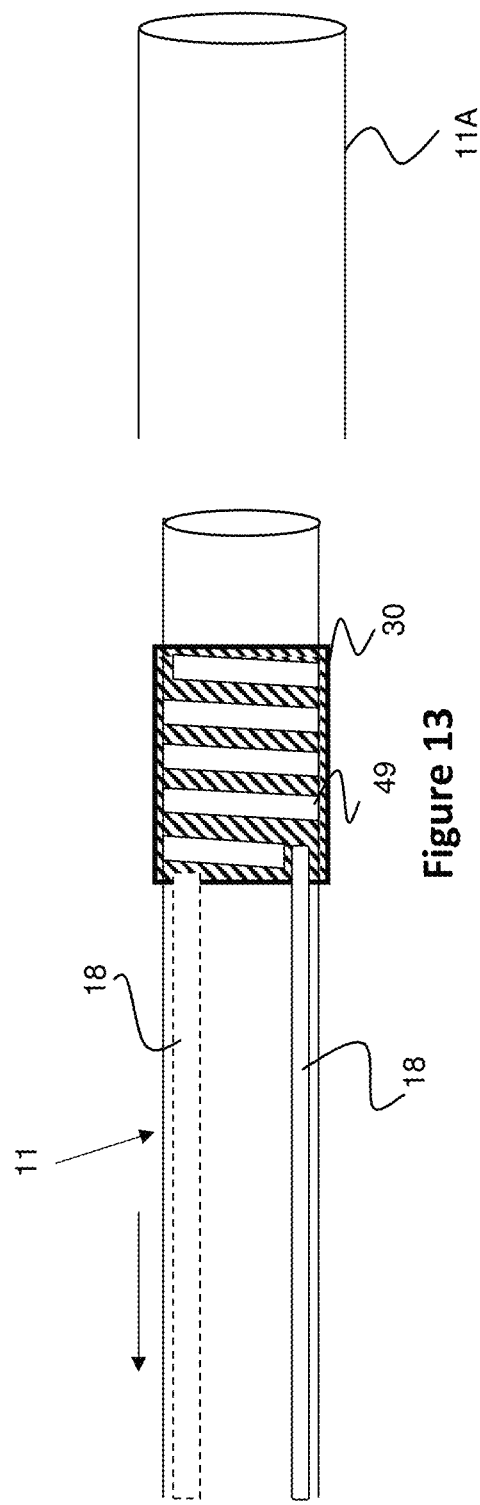

CATHETER CIRCUIT

RELATED APPLICATIONS

This application is a continuation of and claims priority to U.S. patent application Ser. No. 15/169,588 filed May 31, 2016 entitled Catheter Circuit, which claims benefit of and priority to U.S. Provisional Application Ser. No. 62/168,525 filed May 29, 2015 entitled Hyptotube Circuit for a Catheter, both of which are hereby incorporated herein by reference in their entireties.

BACKGROUND OF THE INVENTION

One aspect of the invention relates to a catheter comprising a structural reinforcement such as a braid, and utilizing the structural reinforcement elements to convey current and/or signals in the catheter.

Another aspect of the invention relates to a circuit system which can be used in an interventional device such as a catheter.

Typical circuits utilize a positive and negative pole and thus typically require two sets of wires for a supply and return path for current. Circuit systems used with catheters also utilize such an arrangement, or utilize the patient himself as the ground. The typical arrangement utilizes sets of wires running from the proximal to the distal end of the catheter.

The embodiments disclosed herein describe a circuit comprised of a first set of connections which provide a powering supply and return bank (i.e. positive and negative), and sensors which feed off the powering supply and return bank located near the sensors. The circuit system can utilize a hypotube and can be used in a number of devices, including a catheter. The hypotube itself can be circuited and can include one or more sensors.

SUMMARY OF THE INVENTION

In one embodiment a circuit system utilizes a terminal bank and one or more sensors which feed off the terminal bank.

In another embodiment a circuit system utilizes a voltage source, a terminal bank, and one or more sensors which connect to the terminal bank.

In another embodiment a circuit system utilizes a hypotube, where the hypotube includes a terminal bank and one or more sensors.

In another embodiment a braided catheter utilizes some of the wires comprising the braid to convey current in a circuit.

In another embodiment a braided catheter utilizes some of the wires comprising the braid to convey signals in a circuit.

In another embodiment a braided catheter utilizes some of the constituent wires comprising the braid to convey current to a terminal bank.

In another embodiment a braided catheter utilizes some of the constituent wires comprising the braid to convey current to a terminal bank, where one or more sensors are connected to the terminal bank.

In another embodiment, a braided catheter comprises multiple wires where some of the constituent wires comprising the braid are used to link to a terminal bank.

In another embodiment, a braided catheter comprises multiple wires where some of the wires are used as a supply and return path for a circuit and some of the wires convey a signal.

In another embodiment, a braided catheter comprises multiple wires where some of the wires are used as a supply and return path for a circuit and some of the wires convey a signal between one or more sensors and a user interface.

In another embodiment, a braided catheter comprises a hypotube.

In another embodiment, a braided catheter comprises a hypotube, where the hypotube contains a terminal bank.

In another embodiment, a braided catheter comprises a hypotube, where the hypotube contains a terminal bank and one or more sensors.

In another embodiment a powered catheter includes a hypotube.

In another embodiment a circuit includes a hypotube, where the hypotube contains a terminal bank and one or more sensors.

In another embodiment a powered catheter includes a hypotube, where the hypotube contains a terminal bank and one or more sensors.

In another embodiment a powered catheter includes a variable coil detachment system.

In another embodiment a powered catheter includes a catheter distal tip detachment system.

In another embodiment a powered catheter includes a steerable guidewire system.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which:

FIGS. 12 and 13 illustrate a catheter with a hypotube connected to a plurality of structural wires that supply power so as to allow selective detachment of a distal portion of a catheter.

DETAILED DESCRIPTION

Figure 1:
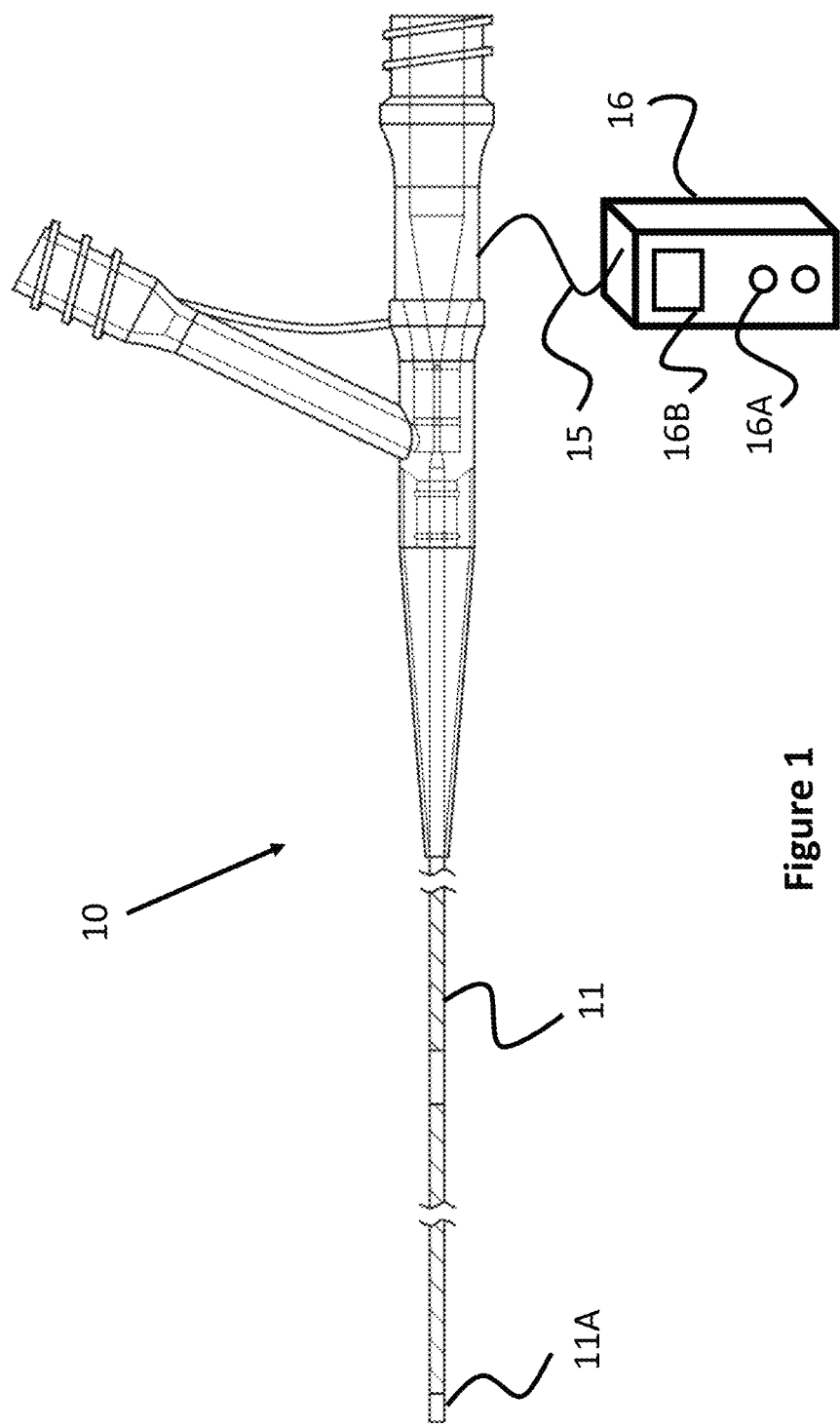
FIG. 1 illustrates a catheter and catheter interface according to the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

It should be understood that a variety of different embodiment and/or variations on components are described herein. It is the intention of this application that each of these embodiments and components can be used and/or interchanged with each other. Therefore, while a specific embodiment may not specify a feature of another embodiment described herein, such a combination is contemplated and included in the present invention.

FIG. 1 illustrates a catheter 10 (or alternately a microcatheter) that delivers power and data through structural wires that make up the elongated tubular portion 11 of the catheter 10. The catheter 10 is connected to an interface 16 that provides power and/or data to and from the catheter via a cable 15. By allowing the structural wires to be used for power/data, the catheter size or diameter can be minimized. Additionally, a plurality of electrically powered components (e.g., sensors) and even circuitry can be used in the distal end 11A (or other locations) in the catheter 10.

While some of the embodiments of the present invention may be described in terms of powering and obtaining data from electrical components such as sensors, it should be understood that a variety of different powered elements are possible. For example, heater coils, mechanical latches, and similar powered implant detachment mechanisms can be powered according to the present invention. In other examples, other powered elements may include imaging systems, pressure sensing, temperature sensing, and oxygen sensing.

Figure 2:
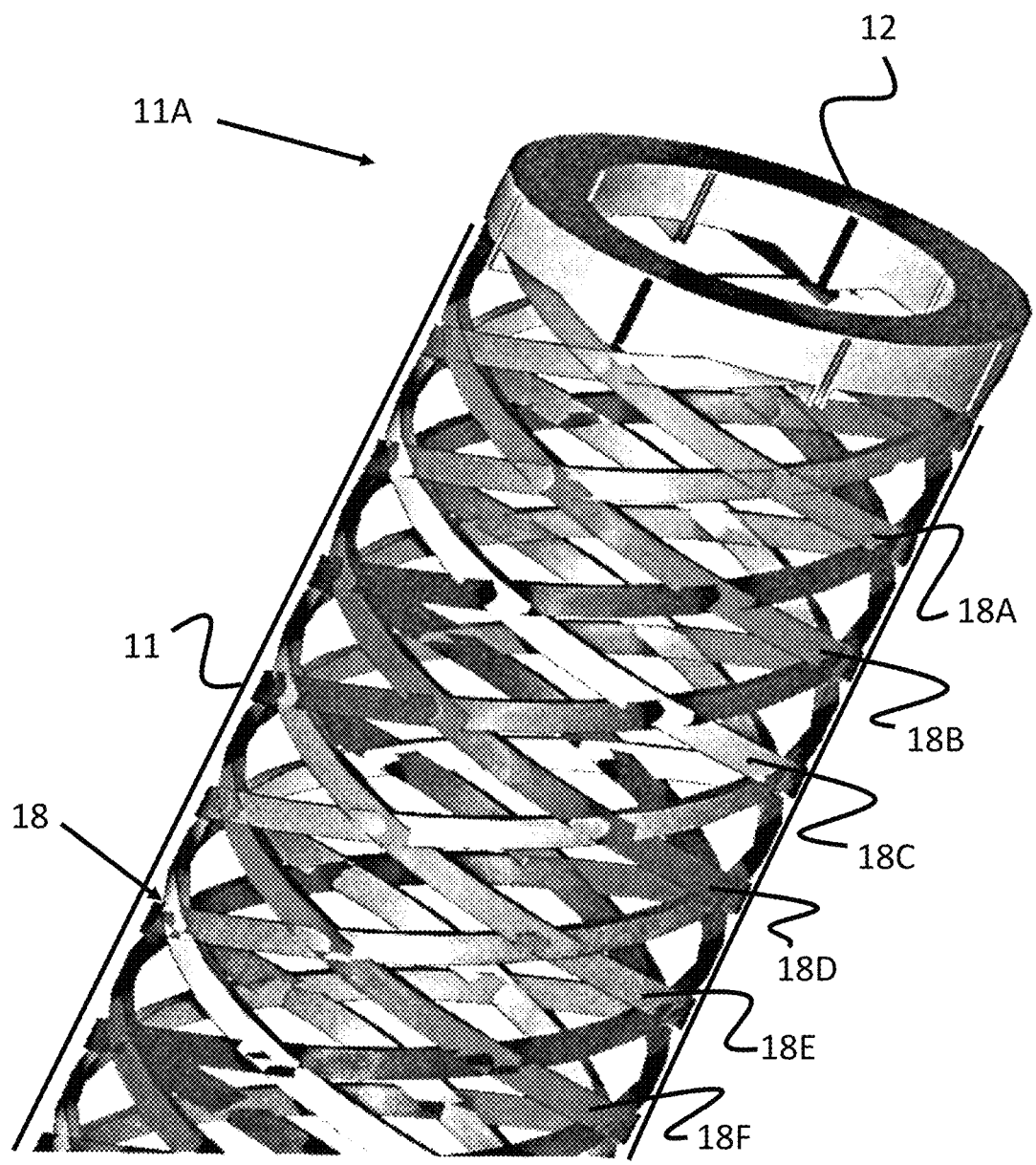
FIG. 2 illustrates a cutaway view of an elongated tube of a catheter having a plurality of braided structural wires that are configured to delivery electrical signals between a distal end of the catheter, according to the present invention.

FIG. 2 illustrates a plurality of braided structural wires 18 that are part of the elongated tubular portion 11 of the catheter 10 that terminate with and connect to a distally located receptacle 12. These wires 18 provide structural support to the elongated tubular portion 11 and also can be used to deliver electrical power and/or data to the proximal end of the catheter 10. The braid of FIG. 1 is comprised of 8 wires (18A-18F) braided in a tubular shape. The braided wires 18 can be located in several different positions as part of the elongated tubular portion 11, such as 1) on an outer surface of the tubing of the elongated tubular portion 11, 2) "sandwiched" between two or more layers of the tubular portion 11 (i.e., not exposed on an interior or exterior of the tubing), and 3) located along the inner surface of the tubular portion 11 so as to be exposed to the interior passage of the tubular portion 11.

Figure 3A:
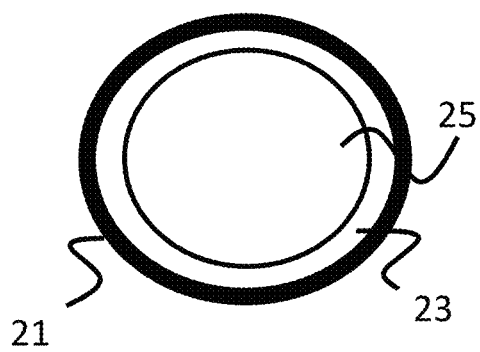
FIGS. 3A and 3B illustrate example cross sections of structural wires that delivery electrical signals according to the present invention.

In one embodiment shown in FIG. 3A, the braided structural wires 18 may be a metal material 25 that is structurally suitable for a catheter (e.g., nitinol or stainless steel) and are coated with a highly conductive layer 23 (e.g., gold) and then coated in an electrical insulation 21 (e.g., polyamide).

Figure 3B:
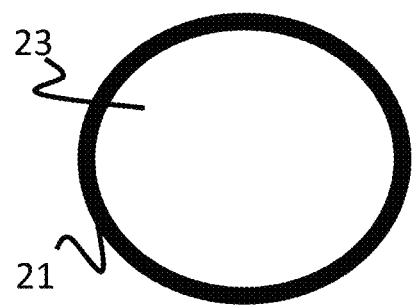

In another embodiment shown in FIG. 3B, the braided structural wires 18 comprising the tubular braid are made entirely of a conductive material 23 (e.g., gold) in order to efficiently convey the current/signal, and further includes an electrically insulating coating 23 preventing discharge of the current/signal while it is being conveyed. While the wires 18 are depicted as having a round or circular cross section in FIGS. 3A and 3B, other shapes are also possible, such as relatively flat, oval, rectangular, and square.

Figure 4:
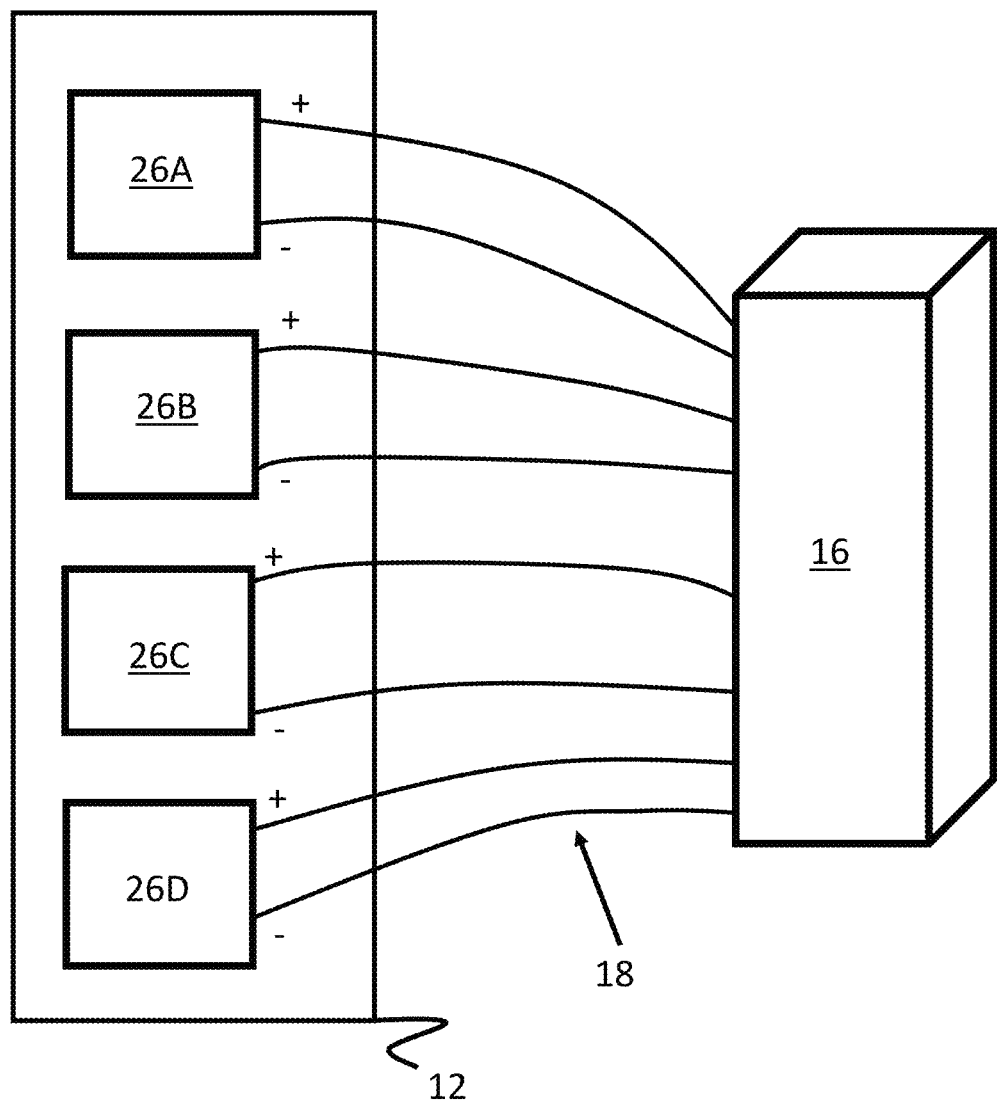
FIG. 4 illustrates a plan view of an interface powering several sensors located at a distal end of the catheter.

FIG. 4 illustrates an abstract schematic diagram of an example circuit system having four electrical components (26A-26D) and a plurality of structural wires 18. Each electrical components 26A-26D is connected to two wires that are connected to a positive and negative terminal of a power source in the interface 16, which thereby supplies power to the electrical components. In this respect, the 8 wire example shown in FIG. 2 can be used to power all of the electrical components and to communicate data back to the interface 16. Similarly, a 10 wire braid would allow 5 electrical components, and a 16 wire braid would allow 8 electrical components since each electrical components would require 2 wires 18 to complete the circuit. In this respect, any number of wires can be used, such as 2, 4, 6, 8, 10, 12, 14, 16, and 18.

Figure 5:
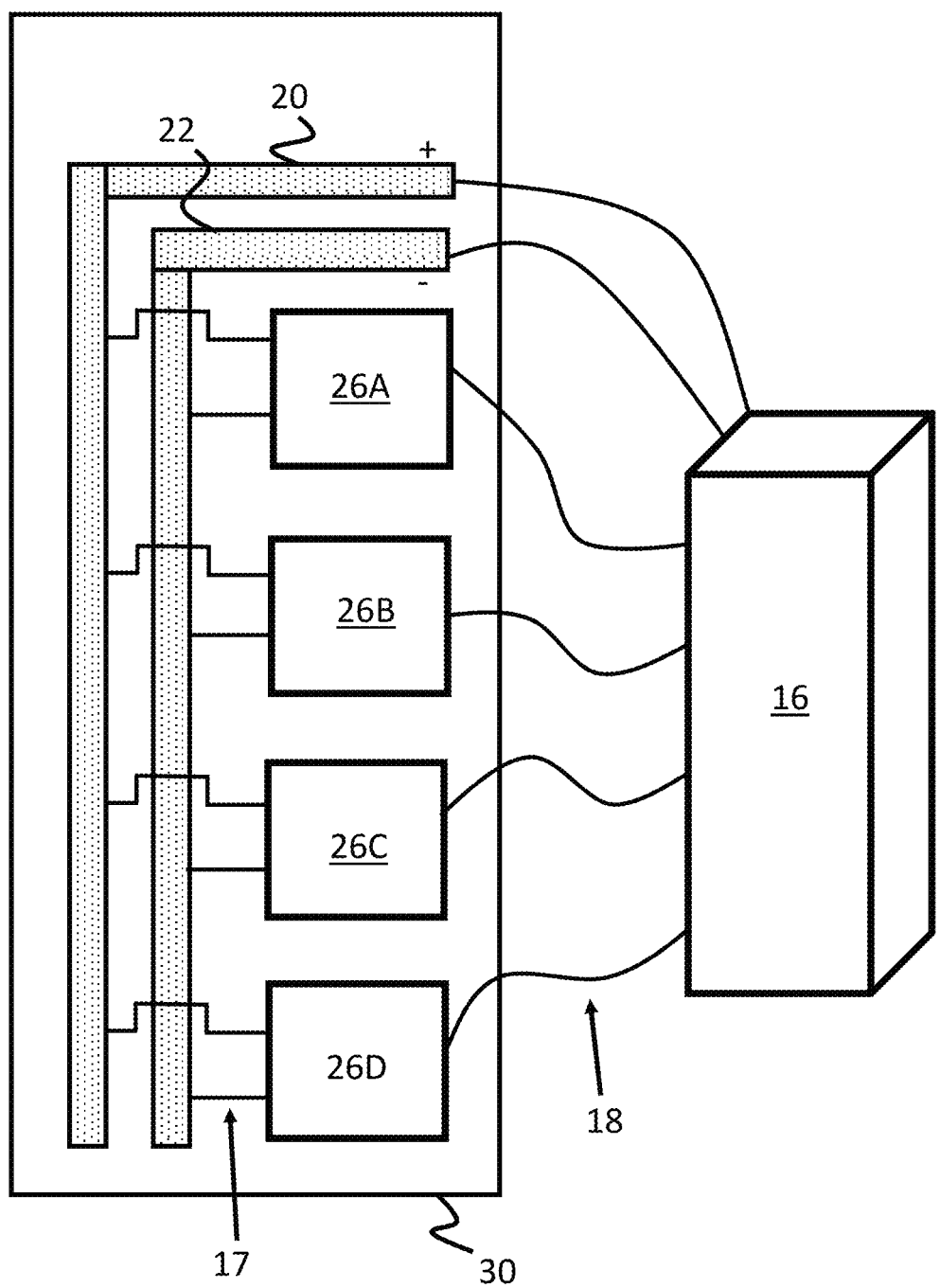
FIG. 5 illustrates an interface powering several sensors via only two power wires and transmitting data signals via a plurality of data wires.

FIG. 5 illustrates another embodiment of a circuit configuration in which only two of the wires 18 provide power via a positive and negative voltage source (e.g., battery) of the interface 16. The wires connect to separated electrical terminals 20 and 22 which are located at or near the distal end 11A of the catheter 10. The electrical components 26A-26D are each connected to these terminals 20, 22 via wires 17 (or any other electrical path), allowing power to be supplied from the interface 16 to each of the electrical components.

The data or signal from each of the electrical components 26A-26D is then conveyed from the electrical components to the user interface via one of the braided wires 18 of the catheter 10. In this way, for example, an 8-wire braid can utilize up to 6 electrical components instead of 4 electrical components. Similarly, a 10-wire braid could utilize up to 8 electrical components (two wires used for the positive and negative terminal connection, and the balance of the wires used to connect each electrical components), a 12-wire braid could utilize up to 10 electrical components, and so on.

It should be understood that some electrical components (such as sensors) require only two power wires to operate and send back data (e.g., such as a thermistor in which changes in resistance on the wires is measured), while other electrical components or sensors require one or more additional wires to convey data (e.g., three wires total). As such, the number of wires used in each of these embodiments also depends on the type of electrical components used.

The user interface 16 preferably acts as a point of control for the user (e.g., press a button 16A) to effect an outcome at the other end of the system (e.g., detach an implant or a distal portion 11A of the catheter 10). Where the electrical components are used for sensing the physiological conditions of the vessel (e.g., pressure or temperature), the user interface may have a display 16B (as well as the underlying CPU/microprocessor, memory, and software to process data and drive the display) indicating the particular physiological condition which is observed. The user interface 16 also preferably contains the voltage source for the circuit, in one example via a battery with a positive and negative terminal.

Figure 6:
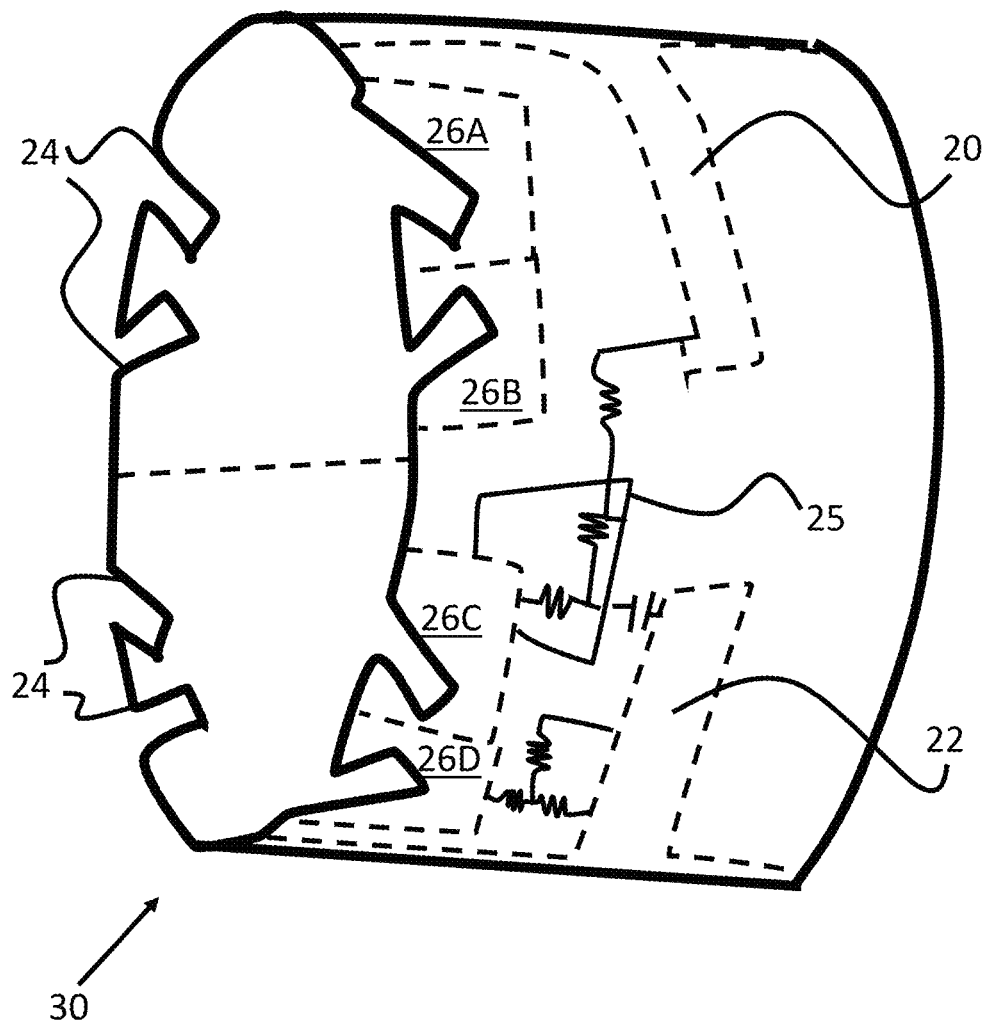
FIG. 6 illustrates an example of a hypotube having a plurality of sensors, connection points and circuit paths.

In one embodiment, the terminal banks and electrical components configuration of FIG. 5 can be formed by a hypotube located near the distal end of a catheter 10, similar to receptacle 12 of FIG. 2. This can be visualized by taking the circuit concept of the distal part of the circuit of FIG. 5 (i.e. the left side of the figure, comprising the terminal banks 20, 22 and electrical components 26A-26D) and configuring it into a cylindrical or circle shape. FIG. 6 illustrates a hypotube representation 30 of such a circuit. The hypotube 30 contains a plurality of notched or cut-out areas 24 which the distal end of the braid wires 18 connect to and/or otherwise mate within. The wires 18 of the braid can be welded or otherwise electro-mechanically joined to the cut-out sections 24 to create a snug connection with the hypotube 30.

The hypotube 30 may also contain embedded circuitry 25. This circuitry 25 may connect to the electrical components 26A-26D, so as to provide additional functionality and/or processing of electrical components signals. This circuitry 25 may also connected to the positive and negative voltage terminal banks 20, 22, as indicated by element 26 in FIG. 5, so as to obtain power for the circuitry 25.

The hypotube 30 may be cut (e.g., laser cut) into a pattern to include the cut-out sections 24. The hypotube 30 is preferably made of materials which are highly conductive, have high mechanical strength, and allow for easy termination/connectivity of other wires and materials. In one example, the hypotube is comprised of a gold plated polyimide and additional laser cuts can be performed to help shape the path of the different electrical paths/circuits. Once a first series of cuts are created, the hypotube is coated with an electrically isolating material, such as parylene, which also acts to bond the circuit paths where the laser cut was made. Parylene strikes a balance between conformal coating properties and high tensile strength, however other materials exhibiting similar characteristics may also be used. Additional laser cuts can be further made to complete any necessary electrical/circuit paths. The parylene insulation may also help hold the hypotube together, thus the circuit cuts are completed after the insulation is added to the preliminary circuit cuts. Once the circuit route is completed, another round of Parylene coating is undertaken to fully encapsulate the component. A final laser cutting process is undertaken where the coating is removed or ablated at key locations in order to allow for the addition of additional wires as resistors within the circuit paths. The hypotube 30 in this form functions in a similar manner to a traditional printed circuit board.

The hypotube circuit can be used for a number of purposes. For example, components can be added to the hypotube 30 itself to allow for signal conditioning or processing at the site of an electrical components instead of at the user interface. In one example, small wires of various resistive properties can be added to create a Wheatstone bridge to increase sensor accuracy. An operational amplifier could also be integrated on the hypotube circuit 25 to improve sensor values.

A wire (e.g., a catheter structural braid wire 18) connects the sensor to the proximal user interface to relay the signal. Much of the signal processing or signal conditioning could be done on the hypotube circuit itself through the methods discussed. Alternatively or additionally, signal processing could also be done on the user interface.

The hypotube 30 may also include a number of signal processing elements, such as operational amplifiers, signal filtering, etc. as part of the circuit 25. One advantage of doing the signal processing in the hypotube 30 itself instead of in the user interface 16 is that the user interface resources could be freed up for other purposes. Additionally, since signals may degrade when conveyed over a distance, the signal can be cleaned up at the distal part of the system before being sent back to the user interface 16, thus reducing the effect of signal degradation on system operation.

One advantage of the circuit concept, as described earlier, is that the circuit 25 and its connection to one or more of the electrical components 26 is completed at the distal portion 11A of the catheter 10, instead of allowing each of the electrical components 26 to have its own wires 18 connected to the interface 16. Hence, the catheter tube 11 may be formed to have a relatively smaller outer diameter.

The electrical components 26 may be used for a number of functions, such as an imaging system, pressure sensing, temperature sensing, oxygen sensing, or any number of additional systems used with powered catheters/microcatheters. The electrical components may also be used as part of an embolic coil detachment system, and/or a detachable catheter tip system, and/or a steerable guidewire system.

Figure 7:
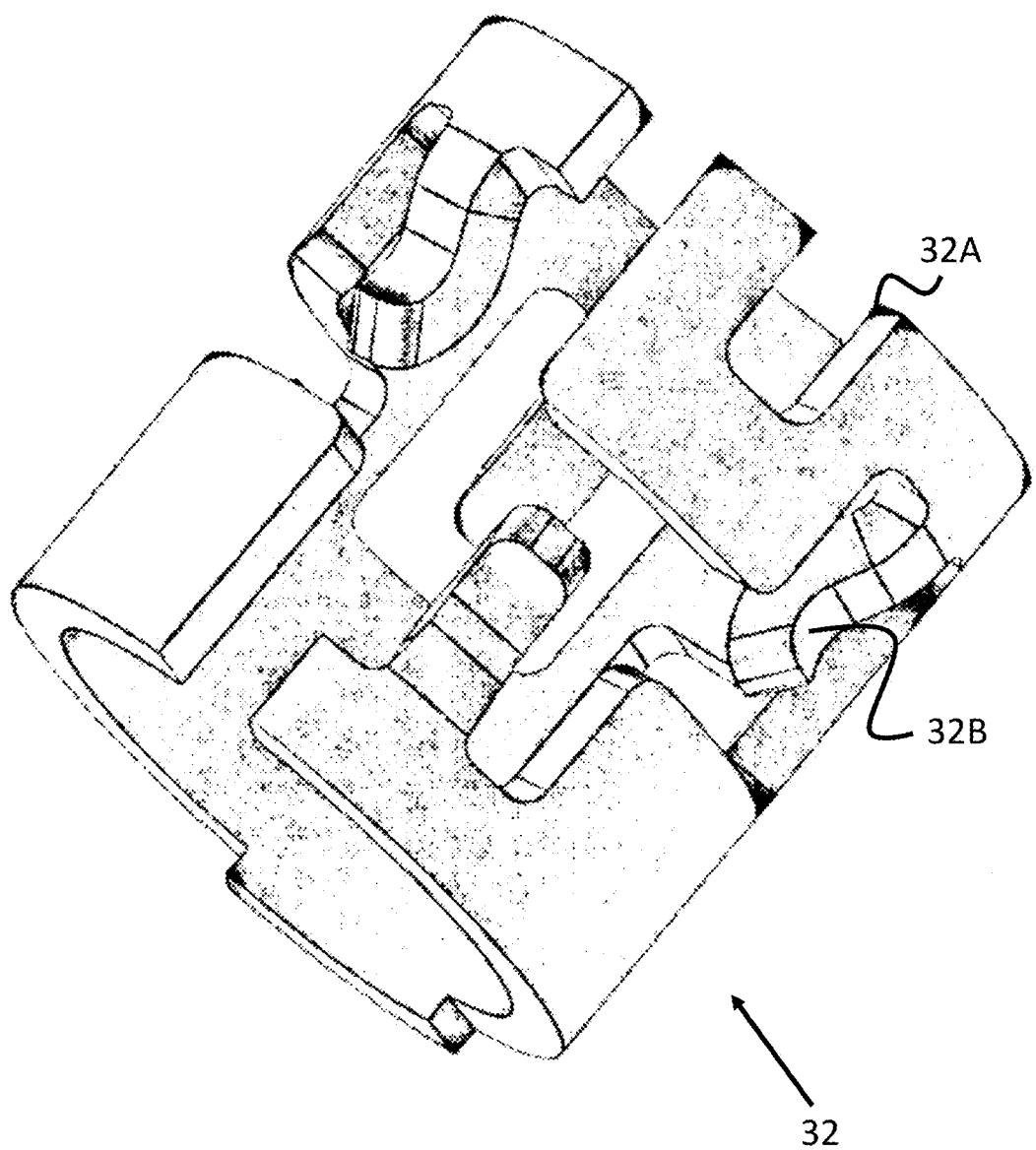
FIGS. 7 and 8 illustrate an alternate embodiment of a hypotube having a plurality of electrical contacts arranged to contact portions of a pusher or implant located within the passage of the catheter.
Figure 8:
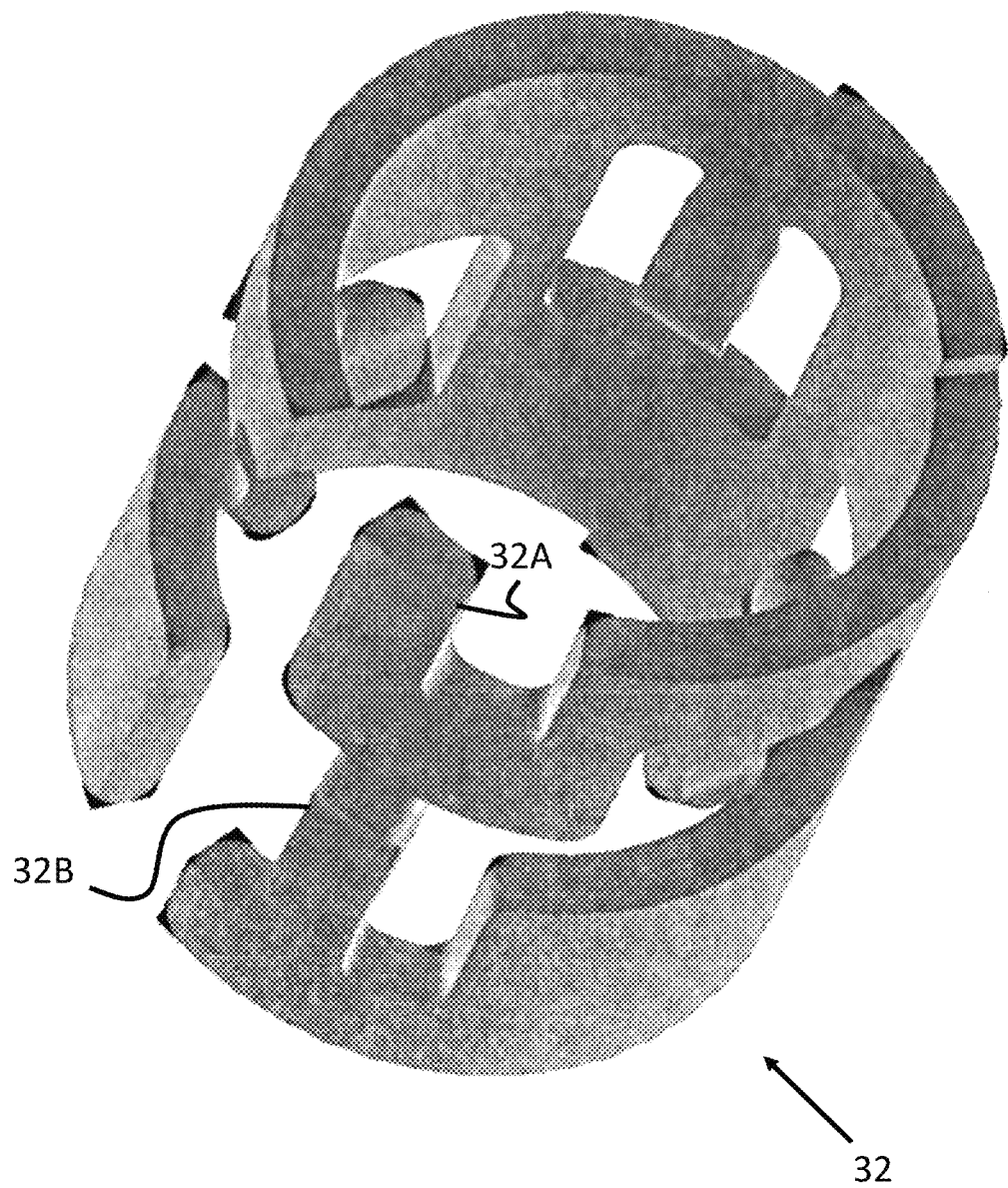

FIGS. 7 and 8 illustrate an alternate structure for a hypotube 32, similar to that of the hypotube 30. In this respect, the hypotube 32 includes one or more notches 32A and a plurality of elongated finger contacts 32B that are each angled or bent inwardly into the hypotube 32. In this respect, power can be supplied to the contacts 32B which, when in contact with electrical contacts on an inner catheter or pusher can cause the catheter or pusher to perform a function, such as detach an implant via a heater or mechanical mechanism.

Figure 9A:
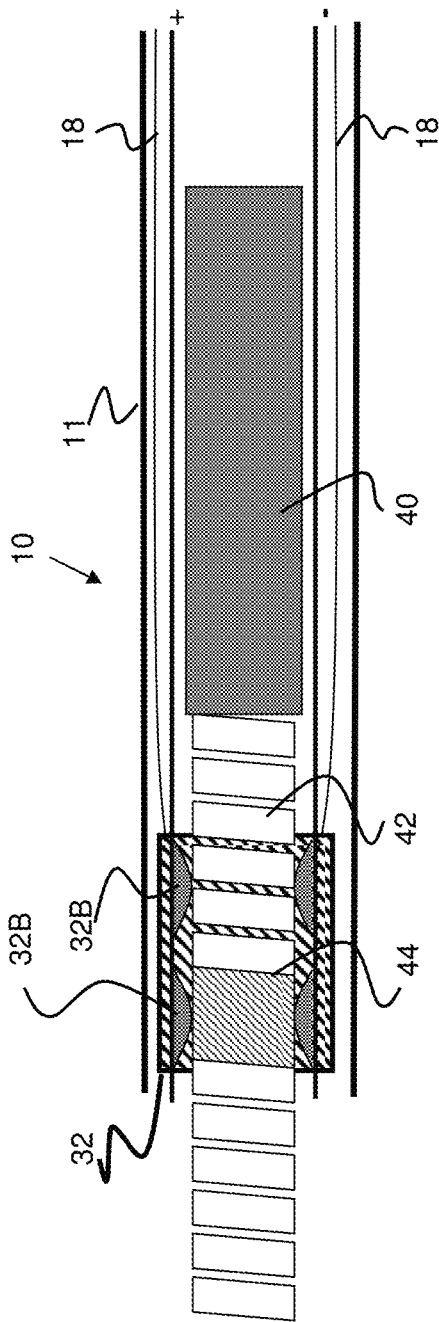
FIGS. 9A and 9B illustrate a catheter having a hypotube with electrical contacts connected to a plurality of structural wires that supply power and that are configured to contact portions of an implant.
Figure 9B:
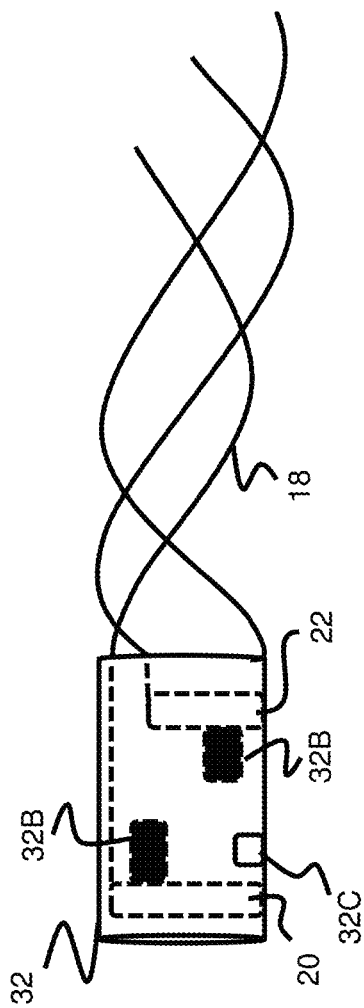

FIGS. 9A and 9B illustrate one example use of a hypotube 32 having contacts 32B used to detach an embolic coil 42 similar to that disclosed in U.S. application Ser. No. 14/578, 106, which is hereby incorporated by reference. The hypotube 32 includes a distal power terminal 20 and a proximal terminal 22 that are connected to one or more distal or proximal contacts 32B, respectively. The embolic coil 42 has one or more detachment points 44 at select locations along the coil 42. When the electrical contacts 32B align with the embolic coil 42 and the detachment point 44 the interface 16 may indicate or display the alignment. Once the user has received an alignment signal, a desired action can be actuated, such as pressing a button to initiate detachment of the coil 42 at the detachment zone 44 from the pusher 40. Since the hypotube 32 can support multiple electrically powered components, a sensor 32C may also be included on the hypotube 32, providing functionality such as detachment detection, temperature sensing, or imaging.

Figure 10:
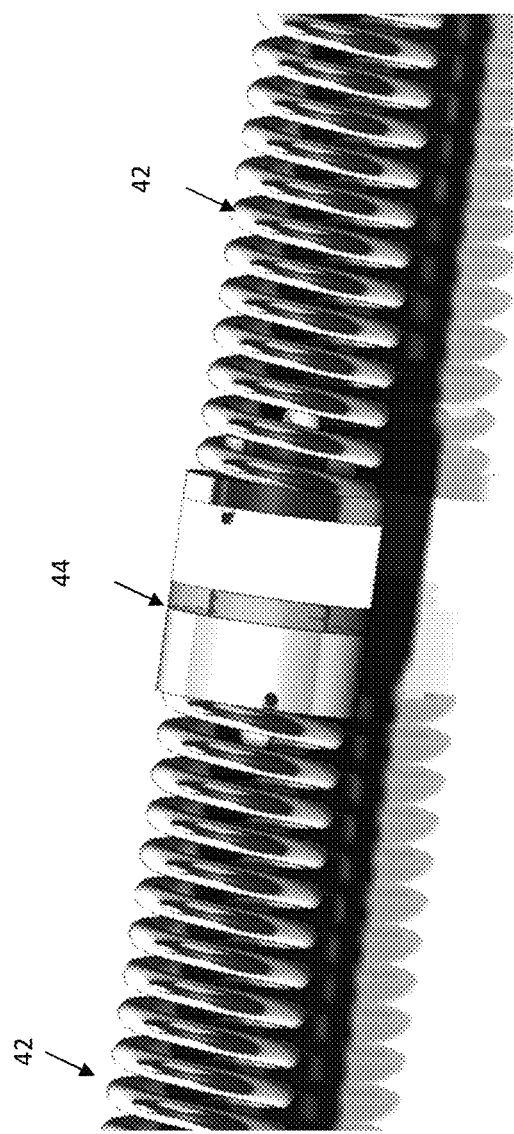
FIGS. 10 and 11 illustrate an embolic coil having a detachment location.
Figure 11:
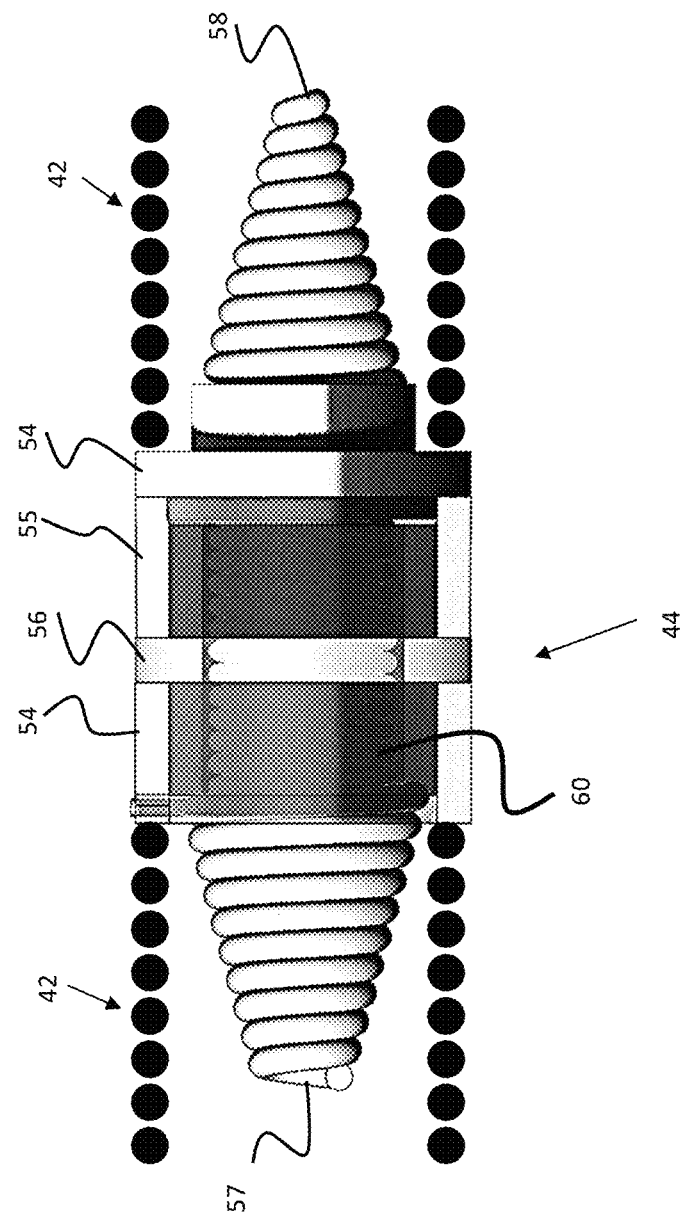

FIGS. 10 and 11 illustrate a more specific example of the detachment point 44 of the embolic coil. Two conductive cylinders or sleeves 54 and 55 are mated to a proximal and distal end of an insulating sleeve 56 via adhesive or glue. The conductive sleeves 54 and 55 are composed of a conductive material, such as a 92/8 ratio platinum/tungsten material.

Heater 60, which can be a coil of wire, spans the area between the proximal and distal conductive sleeves 54 and 55, connecting its ends to each of the sleeves, allowing current to pass through each of the components. Hence, when properly aligned with the proximal and distal contacts 32B of the hypotube 32 and current is applied, the heater coil 60 will increase in temperature, melting the adhesive of the insulating sleeve and causing the distal portion of the embolic coil 42 to detach. Springs 57 and 58 allow for attachment of a monofilament or tether to help prevent stretching of the embolic coil. In an alternate embodiment, a tether may connect between the two springs 57, 58 so as to hold the two segments of the embolic coil 42 together and therefore can be broken by the heater 60 to cause detachment.

In another one example similar to that disclosed in Ser. No. 14/578,106, a steerable guidewire system utilizes spaced positive and negative electrical contacts on a hypotube, similar to that describe in FIGS. 9A and 9B which electrically interact with a bimetallic guidewire to angle a distal end of the guidewire to enable navigation of the guidewire through the vasculature.

As previously discussed, the hypotube 30 and its circuitry can be used to power a heater coil in the catheter 10. In one example FIGS. 12 and 13 disclose a catheter 10 having a detachable distal end tip 11A that is similar to the embodiments disclosed in U.S. application Ser. No. 14/578,020 and hereby incorporated by reference. The hypotube 30 is located at a distal portion of the elongated tubular portion 11 and an adhesive 48 maintains the distal end tip 11A to the elongated tubular portion 11. The user can initiate a detachment sequence (e.g., push a button on the interface 16) to activate the heater 49 and melts the adhesive 48 to effect detachment of the distal end tip 11A of the microcatheter 10 for various reasons (e.g., during delivery of a liquid embolic where there is danger of the distal tip 11A of the catheter getting glued into the vasculature). Similar to the previous example, the hypotube 30 connects to the braided structural wires 18 and provides electrical pathways to the heater 49. In this example, the heater 49 may be located adjacent to or even be connected to the inner surface of the hypotube 30.

Figure 14:
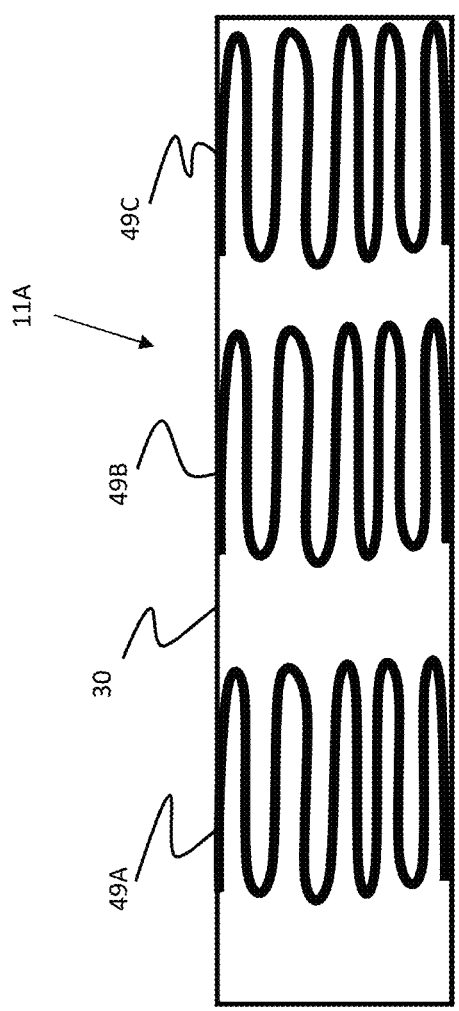
FIG. 14 illustrates a hypotube having a plurality of heater coils.

FIG. 14 illustrates an alternate embodiment of the hypotube 30 of FIG. 13, but instead of connecting to a single heater 49, the hypotube 30 connects to a proximal heater coil 49A, a middle heater coil 49B, and a distal heater coil 49C. The hypotube 30 can be connected to three discrete pairs of wires 18 and electrical paths on the hypotube 30, allowing each of the heater coils to be individually activated.

Figure 15:
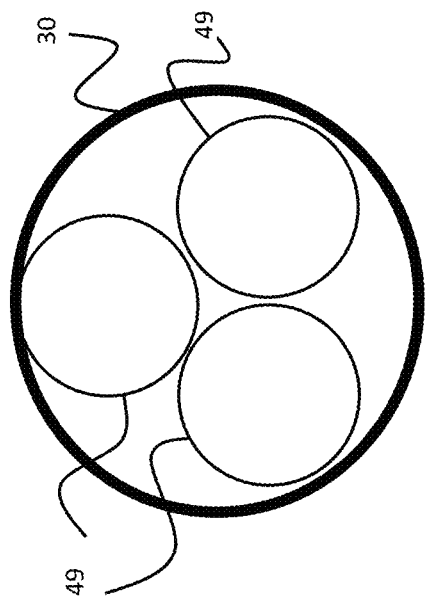
FIG. 15 illustrates a hypotube having a plurality of heater coils.

FIG. 15 illustrates a hypotube 30 with multiple heater coils 49, similar to that of FIG. 14, except that the coils are located parallel and adjacent to each other. In this regard, the hypotube 30 may be located either in a catheter or within a pusher sized for movement within a catheter.

Alternately, the user interface may contain multiple batteries, allowing multiple terminal banks on the hypotube which are connected to the multiple batteries. In another alternative, multiple batteries are used, allowing one battery to provide the terminal bank and the other batteries are selectively used for particular systems (i.e. one battery solely used to power the terminals for the variable coil detachment system, and/or one battery solely used to power the terminals for the detachable tip catheter system). Thus, for example, there could be one positive contact and two negative contacts spaced out at different intervals to interact with the different systems. Similarly, there may be one negative contact and two positive contacts spaced apart at different intervals to interact with the different systems. In one example, the electrical components could control the operation of the exact system in use (i.e. variable detachment, detachable tip, steerable guidewire, or another system) via the integrated circuitry on the hypotube and the signal which is sent to the user interface via the wire braid, as discussed earlier. In another example, the distal hypotube electrical components would be unnecessary if the braid wires are solely used to convey current from the battery as opposed to a signal from electrical components. In this example, the user interface itself would have the circuitry for the various systems and the wires which are used to convey the current between the proximal and distal ends of the catheter are also used to convey the signal from the user interface (i.e. convey the signal input to detach the embolic coil, or detach the catheter tip, or deflect the guidewire tip).

The embodiments and systems described herein offer many advantages in creating a powered catheter system. The following is a non-exhaustive list. One of the main advantages of the system is using the catheter braid itself to convey current, thus providing a useful secondary benefit to the catheter braid besides structural reinforcement of the catheter. Another advantage of the system is using two of the catheter braid wires to power the terminal banks on the hypotube at the distal end of the catheter, and having the electrical components directly connect to the terminal banks on the hypotube itself, thus only requiring one wire to connect the electrical components to the user interface since the electrical components are powered on the hypotube itself. Another advantage of the system is utilizing the distal hypotube as a circuit system, and the ability to allow signal processing to be done on the hypotube itself via the integrated circuitry, instead of at the proximal end of the system. Signals can degrade over a long distance, so offering signal processing at the source of the signal offers some advantages in and of itself. Another advantage is the ability to combine several powered catheter functionalities without requiring a large number of wires to convey all the signals.

In other embodiments, the system described herein would not need a separate negative terminal source and the patient himself could be used as the ground to complete the circuit. Thus, in one example, the proximal part of the system would just contain a positive charge source, a wire would run the current to the distal end of the system and the patient himself would comprise the ground. The distal end of the system would still utilize all the circuitry with the electrical components, but this would allow for an additional electrical component since only one wire would be needed to convey the current since the patient provides the ground.

In other embodiments, an alternate current voltage source could be used instead of a direct current voltage source.

In other embodiments, the wiring for the catheter system would not utilize a catheter braid (i.e. if the catheter does not utilize any braiding) but consists of wires which are external or internal to the catheter surface, or integral between layers of the catheter tubing. In other embodiments reinforcement coil(s) or ribbon(s) could be used instead of a braid.

In other embodiments the terminal banks could be replaced with a capacitor. The capacitor could then store the charge from the voltage source.

The embodiments described include a circuit system. The circuit system can be used on a number of devices including interventional devices, including a catheter or microcatheter or other delivery device.

The embodiments described utilize the structural reinforcement layer of a catheter (generally described as a braid) to conduct current between two ends of the catheter. Though the term braid is used, the term should be interpreted broadly so as to describe any structural layer, thus the term braid may include coils, ribbons, and other structural components commonly used in catheters.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A catheter comprising:
   an elongated tubular portion having a proximal end and a distal end;
   a circuit system located near the distal end of the elongated tubular portion, the circuit system comprising:
   a hypotube located at the distal end of the elongated tubular portion and which comprises an electrically conductive material;
   a positive terminal bank and a negative terminal bank terminal bank; and,
   a plurality of electrical components;
   wherein the hypotube, the positive terminal bank, the negative terminal bank, and the plurality of electrical components are in a form of a cylindrical shape; and,
   wherein the hypotube is cut into a pattern forming electrical paths that electrically connect to the positive terminal bank, the negative terminal bank, and the plurality of electrical components.

2. The catheter of claim 1, further comprising a proximal interface powering the circuit system.

3. The catheter of claim 2, further comprising a first wire linked to the interface and the positive terminal bank, and a second wire linked to the interface and the negative terminal bank.

4. The catheter of claim 2, wherein each of the plurality of electrical components is connected to a wire which is connected to the proximal interface, such that each electrical component is connected to a different wire.

5. The catheter of claim 4, wherein each of the plurality of wires is a braided structural wire that is part of the elongated tubular portion.

6. The catheter of claim 1, wherein the hypotube is further coated with an electrically isolating material.

7. The catheter of claim 6, wherein the electrically isolating material is parylene.

8. The catheter of claim 6, wherein the hypotube is encapsulated with the electrically isolating material.

9. The catheter of claim 6, wherein the electrically isolating material comprises a first layer and a second layer.

10. The catheter of claim 1, wherein the hypotube includes a plurality of notched regions at one end of the hypotube.

11. The catheter of claim 10, wherein each of the plurality of electrical components includes a notched region.

12. The catheter of claim 10, wherein the plurality of notched regions are positioned along a proximal edge of the hypotube.

13. The catheter of claim 10, wherein each of the plurality of notched regions is connected to a wire and each wire is connected to a proximal interface.

14. The catheter of claim 1, wherein each of the plurality of electrical components comprise an electrical component that reduces sensor signal degradation.

15. The catheter of claim 14, wherein each of the plurality of electrical components comprise an operational amplifier, a signal filter, a signal processor, or a Wheatstone bridge.

16. A catheter comprising:
    an elongated tubular portion having a proximal end and a distal end; the elongated tubular portion forming a passage extending between the proximal end and the distal end;
    a circuit system located near the distal end of the elongated tubular portion, the circuit system comprising:
    a hypotube located at the distal end of the elongated tubular portion and which comprises an electrically conductive material;
    a positive terminal bank and a negative terminal bank terminal bank; and,
    a plurality of electrical components;
    wherein the hypotube, the positive terminal bank, the negative terminal bank, and the plurality of electrical components are in a form of a cylindrical shape positioned around the passage of the elongated tubular portion; and,
    wherein the hypotube is cut into a pattern forming electrical paths that electrically connect to the positive terminal bank, the negative terminal bank, and the plurality of electrical components.

17. The catheter of claim 16, wherein the hypotube is coated with an electrically isolating material.

18. The catheter of claim 17, wherein the hypotube comprises a metal plated polyimide material.

19. A catheter comprising:
    an elongated tubular portion having a proximal end and a distal end; the elongated tubular portion forming a passage extending between the proximal end and the distal end;
    a plurality of electrical wires located within a wall of the tubular portion and extending between the proximal end and the distal end of the elongated tubular portion;
    a circuit system located near the distal end of the elongated tubular portion, the circuit system comprising:
    a hypotube located at the distal end of the elongated tubular portion and which comprises an electrically conductive material;
    a positive terminal bank and a negative terminal bank terminal bank that are connected to the plurality of electrical wires; and,
    a plurality of electrical components;
    wherein the hypotube, the positive terminal bank, the negative terminal bank, and the plurality of electrical components are configured into a cylindrical shape positioned around the passage of the elongated tubular portion;
    wherein the hypotube is cut into a pattern forming electrical paths that electrically connect to the positive terminal bank, the negative terminal bank, and the plurality of electrical components; and,
    wherein the hypotube is coated with one or more layers of electrically isolating material that isolates the electrical paths formed by the pattern.

* * * * *